US011849951B2

(12) United States Patent
Solorio et al.

(10) Patent No.: US 11,849,951 B2
(45) Date of Patent: Dec. 26, 2023

(54) SYSTEM AND METHODS FOR SUPPLYING SURGICAL STAPLE LINE REINFORCEMENT

(71) Applicant: Cook Biotech Incorporated, West Lafayette, IN (US)

(72) Inventors: Loran Solorio, West Lafayette, IN (US); Steven Cohen, West Lafayette, IN (US); David Tapia, Winston-Salem, NC (US); Bhavin B. Shah, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 145 days.

(21) Appl. No.: 17/443,477

(22) Filed: Jul. 27, 2021

(65) Prior Publication Data
US 2022/0022871 A1   Jan. 27, 2022

Related U.S. Application Data

(60) Provisional application No. 63/057,044, filed on Jul. 27, 2020.

(51) Int. Cl.
*A61B 17/072* (2006.01)
*A61B 50/30* (2016.01)
*A61B 17/00* (2006.01)
*A61B 17/068* (2006.01)
*A61B 50/00* (2016.01)

(52) U.S. Cl.
CPC ........ *A61B 17/07292* (2013.01); *A61B 50/30* (2016.02); *A61B 2017/0053* (2013.01); *A61B 2017/00526* (2013.01); *A61B 2017/0688* (2013.01); *A61B 2050/0065* (2016.02)

(58) Field of Classification Search
CPC .............. A61B 17/07292; A61B 50/30; A61B 2050/0065; A61B 2017/0053; A61B 2017/0688
USPC ............................................ 227/175.1–180.1
See application file for complete search history.

(56) References Cited

U.S. PATENT DOCUMENTS

| 11,141,150 | B2* | 10/2021 | Shelton, IV | ......... A61B 17/072 |
| 2003/0120284 | A1* | 6/2003 | Palacios | ........... A61B 17/07207 |
| | | | | 606/139 |
| 2009/0205986 | A1 | 8/2009 | Baker et al. | |
| 2016/0278776 | A1* | 9/2016 | Shelton, IV | ......... A61B 17/068 |
| 2017/0055981 | A1* | 3/2017 | Vendely | ........... A61B 17/07207 |

(Continued)

FOREIGN PATENT DOCUMENTS

| EP | 3363374 A2 | 8/2018 |
| WO | WO 2005/079675 A2 | 9/2005 |

OTHER PUBLICATIONS

Search Report and Written Opinion in PCT/US2021/070983 dated Nov. 5, 2021.

*Primary Examiner* — Robert F Long
*Assistant Examiner* — Xavier A Madison
(74) *Attorney, Agent, or Firm* — Woodard Emhardt Henry Reeves & Wagner

(57) ABSTRACT

In certain aspects, the present disclosure provides devices for loading a surgical bolster material. In accordance with some forms, the device includes a tray defining a guide channel for receipt of a bolster material. The guide channel may be configured to align and/or direct the device onto which the bolster material is to be loaded onto the bolster material.

22 Claims, 9 Drawing Sheets

(56) References Cited

U.S. PATENT DOCUMENTS

2017/0119386 A1\* 5/2017 Scheib ............. A61B 17/07292
2018/0235626 A1\* 8/2018 Shelton, IV ..... A61B 17/07207

\* cited by examiner

SYSTEM AND METHODS FOR SUPPLYING SURGICAL STAPLE LINE REINFORCEMENT

CROSS REFERENCE TO RELATED APPLICATION

This application claims the benefit of Provisional Patent Application Ser. No. 63/057,044 filed Jul. 27, 2020.

BACKGROUND

The present disclosure resides generally in the field of medicine and in particular aspects to devices and methods that are useful for applying a bolster material to a device for inserting surgical fasteners, e.g. a surgical stapler.

As further background, surgical stapler devices are designed to seal or simultaneously cut and seal an extended segment of tissue in a patient. Some surgical staplers include two stapler arms, a first arm including two or more lines of multiple staples (also called a "cartridge" or "jaw") and a second arm including an anvil or other feature adapted to bend each of the staples into a closed position upon operation of the stapler. So-called "anastomotic" staplers include a surgical blade in the device to sever tissue between the lines of staples. Those without such a cutting blade have been referred to as "non-anastomotic" staplers.

For some medical procedures, the use of bare staples, with the staples in direct contact with the patient's tissue, is generally acceptable. The integrity of the patient's tissue itself will normally serve to prevent the staples from tearing out of the tissue and compromising the seam before healing has occurred. However, in other procedures, the patient's tissue to be sealed is too fragile to securely hold the staples in place. For example, in the case of lung tissue, and in particular diseased lung tissue, the tissue to be stapled is fragile and, in extreme cases, will easily tear through unprotected staple lines. With the growing use of surgical staplers in operations on diseased lung tissues such as bullectomies and volume reduction procedures, it has become increasingly important to take measures to protect fragile tissue from tissue tears due to surgical staples or surgical stapling procedures.

One known protective measure involves the use of a reinforcement or bolster material, wherein the staples are inserted both through the bolster material and the patient's tissue. In many cases, as a preliminary step, the reinforcement material is in some manner applied to the arms of the surgical stapler, e.g. with portions applied to each arm, and the stapler thereafter used to secure tissue of the patient. In some cases, a liquid adhesive is applied to the bolster material to aid in temporarily attaching the bolster material to the surgical stapler. Liquid adhesives may run from the application site causing a variety of complications including: uneven application of the adhesive, misalignment of the bolster material with the surgical stapler, and/or interfering with the operation of the surgical stapler. The present disclosure provides medical devices and methods that are useful for applying bolster material to surgical staplers or other similar surgical fastening devices.

SUMMARY

In certain aspects, the present disclosure provides unique medical articles useful for applying a bolster material to a surgical fastening device such as a surgical stapling device, and related methods. In accordance with some forms of the disclosure, such medical articles have a removable layer protecting an adhesive layer on a bolster material while also being configured to align the bolster material and adhesive layer with an arm of a surgical stapling device. Accordingly, in one embodiment, the present disclosure provides a device for loading a surgical bolster material onto a surgical stapling device. The device comprising a tray defining a guide channel for receipt of a bolster material to be applied to the surgical stapling device, a compressible layer having a first portion compressed by the tray and a second portion extending into the guide channel, a bolster material carried by said compressible layer, an adhesive layer on the bolster material and configured to adhere the bolster material to the stapler, and a peelable protective cover over the adhesive layer. In some forms, the peelable protective cover is peelable from the adhesive layer while the compressible layer and the bolster material are received in the tray with the bolster material in the guide channel. In accordance with certain inventive variants, the bolster material comprises a first lateral edge and a second lateral edge and the first lateral edge of the bolster material and the second lateral edge of the bolster material are uncompressed by the tray. In certain embodiments, the adhesive layer comprises a first lateral edge and a second lateral edge wherein the first lateral edge of the adhesive layer and the second lateral edge of the adhesive layer are uncompressed by the tray.

In some forms, the guide channel is defined by a channel wall. In certain embodiments, the channel wall includes one or more recessed portions such that the guide channel may have a first channel width between opposing faces of the channel wall outside of the recessed portions and a second channel width between opposing portions of the channel wall within the recessed portions such that the second channel width is greater than the first channel width. In accordance with certain inventive variants, the compressible layer has a width between a first lateral edge and a second lateral edge and the compressible layer width is less than the second channel width. In some forms, the compressible layer width is greater than the first channel width such that a portion of the compressible layer rests within the one or more recessed portions. In accordance with some forms, the compressible layer comprises a multi-layer construct comprising one or more layers of bolster support material carried by a core material. In certain embodiments, the core material has a maximum width greater than a maximum width for the bolster support material.

In some forms, the bolster material comprises a first sheet portion and a second sheet portion. In certain embodiments, the first sheet portion of the bolster material is carried on a first side of the compressible layers and the second sheet portion of the bolster material is carried by a second side of the compressible layer. In accordance with some forms, the bolster material comprises a bridge portion connecting the first sheet portion to the second sheet portion.

In accordance with certain embodiments, the compressible layer comprises a detachable region between the first portion and the second portion. In some forms, the bolster material comprises one or more attachment members configured to releasably secure the bolster material to the compressible layer. In accordance with certain inventive variants, the first portion of the compressible layer comprises one or more notches configured to receive and secure the attachment members of the bolster material. In some forms, the attachment members of the bolster material are detachable from the bolster material. In accordance with some forms, the bolster material comprises a collagenous material for example, a naturally derived extracellular matrix material. Thus, in some forms the compressible layer and the bolster material are detachable from the tray, either separately or together. In accordance with certain modes of use as described herein the bolster material may be adhered to a portion of a surgical fastening device, the compressible layer and the bolster material may then be detached from the tray and carried by the surgical fastening device. In some forms, one or more portions of the compressible layer and/or bolster materiel material with the tray after detaching.

In another embodiment, the disclosure provides a method of loading a bolster material onto a surgical stapling device, the method comprising providing a surgical stapling device having a receiving area for receipt of a bolster material, the receiving area including a first surface and a second surface. The method also includes providing a loading device for loading a surgical bolster material onto the surgical stapling device, the device comprising a tray defining a guide channel for receipt of a bolster material to be applied to the surgical stapling device, a compressible layer having a first portion compressed by the tray and a second portion extending into the guide channel, a bolster material carried by the compressible layer, an adhesive layer on the bolster material and configured to adhere the bolster material to the receiving area of the surgical stapling device, and a peelable protective cover over the adhesive layer, the peelable protective cover peelable from the adhesive layer while the compressible layer in the bolster material are received in the tray with the bolster material in the guide channel. The method also comprises removing the peelable protective cover while the compressible layer and the bolster material are received in the tray with the bolster material in the guide channel, and contacting the receiving area with the adhesive layer to adhere to the bolster material to the surgical stapling device. In accordance with some forms, the compressible layer comprises a detachable region between the first portion and the second portion. In certain embodiments, the method further comprises detaching the first portion of the compressible layer from the second portion of the compressible layer. In some forms, the method further comprises removing the surgical stapling device and the bolster material from the loading device.

In another embodiment, the present disclosure provides a method of loading a bolster material onto a surgical stapling device, the method comprising: removing a peelable protective cover from a bolster material, the bolster material received in a guide channel of a loading device, wherein removing the peelable protective cover exposes an adhesive layer on the bolster material; and contacting the adhesive layer to a surgical stapling device to adhere the bolster material to the surgical stapling device.

In some forms of practicing the disclosed methods, the bolster material comprises a first lateral edge and a second lateral edge wherein the first lateral edge of the bolster material and the second lateral edge of the bolster material are uncompressed by the tray. In certain embodiments, the adhesive layer comprises a first lateral edge and a second lateral edge wherein the first lateral edge of the adhesive layer and the second lateral edge of the adhesive layer are uncompressed by the tray.

In some forms of practicing the disclosed methods, the guide channel is defined by a channel wall. In certain embodiments, the channel wall includes one or more recessed portions such that the guide channel may have a first channel width between opposing faces of the channel wall outside of the recessed portions and a second channel width between opposing portions of the channel wall within the recessed portions such that the second channel width is greater than the first channel width. In accordance with certain inventive variants, the compressible layer has a width between a first lateral edge and a second lateral edge and the compressible layer width is less than the second channel width. In some forms, the compressible layer width is greater than the first channel width such that a portion of the compressible layer rests within the one or more recessed portions. In accordance with some forms, the compressible layer comprises a multi-layer construct comprising one or more layers of bolster support material carried by a core material. In certain embodiments, the core material has a maximum width greater than a maximum width for the bolster support material.

In some forms of practicing the disclosed methods, the bolster material comprises a first sheet portion and a second sheet portion. In certain embodiments, the first sheet portion of the bolster material is carried on a first side of the compressible layers and the second sheet portion of the bolster material is carried by a second side of the compressible layer. In accordance with some forms, the bolster material comprises a bridge portion connecting the first sheet portion to the second sheet portion.

In accordance with certain embodiments, the compressible layer comprises a detachable region between the first portion and the second portion. In some forms, the bolster material comprises one or more attachment members configured to releasably secure the bolster material to the compressible layer. In accordance with certain inventive variants, the first portion of the compressible layer comprises one or more notches configured to receive and secure the attachment members of the bolster material. In some forms, the attachment members of the bolster material are detachable from the bolster material. In accordance with some forms, the bolster material comprises a collagenous material for example, a naturally derived extracellular matrix material.

In another embodiment, the present disclosure provides a tray having a guide channel for receipt of a bolster material, the tray comprising: a first tray component defining a first portion of a guide channel for receipt of a bolster material, and a second tray component opposing the first tray component and defining a second portion of said guide channel for receipt of a bolster material, wherein said first and second tray components are joined by one or more friction fittings.

Further forms, objects, features, aspects, benefits, advantages, and embodiments of the present invention will become apparent from a detailed description and drawings provided herewith.

DESCRIPTION OF THE SELECTED EMBODIMENTS

Figure 1:
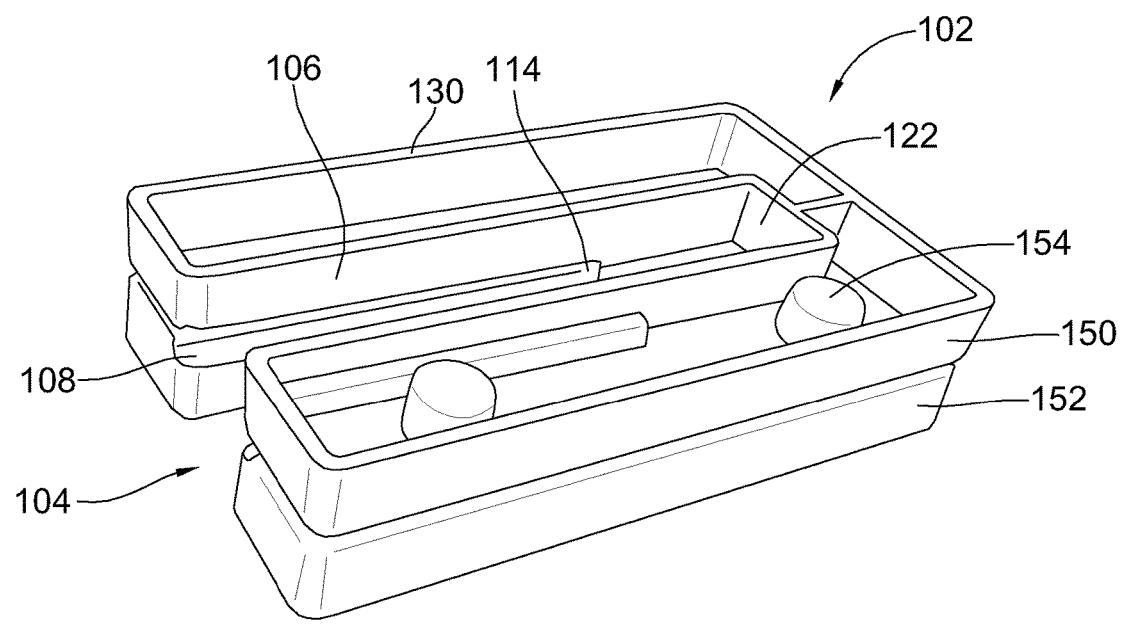
FIG. 1 is a perspective view of one embodiment of a tray for loading a surgical bolster material onto a surgical stapling device as disclosed herein.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

As disclosed above, the present disclosure provides medical articles useful for applying a bolster material to a surgical fastening device such as a surgical stapling device, and related methods. In this regard, aspects of the present disclosure are at times described herein in connection with a surgical stapling device. While this represents an embodiment of the disclosure, it will be understood that the devices of the disclosure may be used in conjunction with a variety of surgical fastening devices that insert fasteners of various designs, including for example one-part and multiple (e.g. two) part staples, tacks, or other penetrating fasteners where bolstering may provide a benefit.

In certain aspects, the present disclosure provides devices for loading a surgical bolster material. In accordance with some forms, the device includes a tray defining a guide channel for receipt of a bolster material. The guide channel may be configured to align and/or direct the device onto which the bolster material is to be loaded onto the bolster material. In certain embodiments, the guide channel may protect an exposed adhesive surface on the bolster material from accidental contact prior to attachment to the intended device. In certain embodiments, the tray may comprise one or more walls defining the guide channel.

In certain embodiments, devices of the present disclosure comprise a tray defining a guide channel. In some forms, the tray may comprise one or more tray components. For example, in certain embodiments the tray is formed by bringing together one or more tray components. In some embodiments, the tray components are identical structures configured to form a tray defining a guide channel when brought together. In some forms, the guide channel is defined by a portion of a first tray component and a portion of a second tray component. In accordance with some forms, corresponding grooves on each of the tray components form the recessed portions of the guide channel wall when brought together.

In some forms, one or more tray components are configured to attach to other tray components. For example, in some forms, the tray components comprise one or more fittings configured to pair with a corresponding fitting on a separate tray components. In some forms, the fittings comprise friction fittings. Thus in certain embodiments, the tray components may be configured with one or more recesses and/or one or more protrusions such that the one or more recesses on a first tray component are configured to receive one or more corresponding protrusions on a second tray component. In embodiments wherein identical tray components are utilized, a tray component may comprise one or more protrusions on a first side and one or more recesses on a second side such that the protrusions and recesses of a first tray component correspond to protrusions and recesses of a second identical tray component when brought together. It is also envisioned that such fittings may comprise use of adhesives and/or heat.

In some forms, the presently disclosed devices are configured to provide a guide channel. In certain embodiments, a guide channel is configured for receipt of a bolster material to be applied to a surgical stapling device. In accordance with some forms, the guide channel comprises a longitudinal opening defined by a channel wall having an open end and a closed end opposite the open end. In use, the channel wall may serve to position one or more arms of a surgical stapling device over a bolster material for loading of the bolster material onto the surgical stapling device. In accordance with some forms, the guide channel has a width between opposing faces of the channel wall. In certain embodiments the channel width is about 0.25 inches to about 0.75 inches, preferably about 0.4 inches to about 0.6 inches, even more preferably about 0.5 to about 0.6 inches. In certain embodiments, the channel has a width of about 0.54 inches. In certain embodiments the channel width is about 6.35 mm to about 19.05 mm, preferably about 10.16 mm to about 15.24 mm, even more preferably about 12.7 mm to about 15.24 mm. In certain embodiments, the channel has a width of about 13.716 mm. In accordance with some forms, the guide channel has a depth from the open end to the closed end. In certain embodiments, the channel depth is about 10 mm to about 100 mm, preferably about 30 mm to about 80 mm. In certain embodiments, the channel depth is about 45 mm. In certain embodiments, the channel depth is about 60 mm.

In accordance with some forms, the present disclosure provides for devices comprising a recessed portion in the channel wall. In some forms, the channel walls may contain one or more recessed portions. In certain embodiments, for example those comprising one or more tray components, the recessed portion comprises a groove at or near the edge of the guide channel, such that when the tray components are combined, the grooves on opposing tray components form a recessed portion of the channel wall. In this way, the recessed portion has an opening width measured along the plane of the channel wall over the opening formed by the recessed portion. In certain embodiments, the recessed portion has an opening width of about 0.05 inches about 0.5 inches, preferably about 0.10 to about 0.25 inches. In certain embodiments, the recessed portion has an opening width of about 0.13 inches. In certain embodiments, the recessed portion has an opening width of about 1.25 mm to about 12.5 mm, preferably about 2.5 mm to about 6.35 mm. In certain embodiments, the recessed portion has an opening width of about 3.3 mm. In some forms, the recessed portion has a depth from the open end of the channel wall to a back wall of the recessed portion. In certain embodiments, the back wall of the recessed portion is generally parallel to the channel wall. In certain embodiments, the recessed portion has a depth of about 0.05 inches about 0.5 inches, preferably about 0.10 to about 0.25 inches. In certain embodiments, the recessed portion has a depth of about 0.135 inches. In certain embodiments, the recessed portion has a depth of about 1.27 mm about 12.7 mm, preferably about 2.54 mm to about 6.35 mm. In certain embodiments, the recessed portion has a depth of about 3.429 mm. In accordance with some forms, guide channel may have a first channel width between opposing faces of the channel wall outside of the recessed portions, and a second channel width measured within the recessed portions. In this way, the second channel width may be greater than the first channel width. In certain embodiments, the recessed portion extends from at or near the guide channel opening, such that the width of the guide channel opening at the recessed portion is greater than the width of the guide channel opening outside of the recessed portion. In certain embodiments, the recessed portion may extend along the length of the guide channel wall. In some forms, the recessed portion may extend along a partial length of the guide channel wall. In some forms, the guide channel is defined by a first wall opposing a second wall, and wherein the guide channel is present on one or both of the first and second wall.

In certain embodiments, the present disclosure provides a compressible layer. In some forms, the compressible layer is configured to support a bolster material within the guide channel. In some forms, the compressible layer may have a first portion which is secured by the tray and a second portion extending into the guide channel. In certain embodiments, the second portion may have a maximum width larger than the first channel width (outside of the recessed portions) but smaller than the second channel width (within the recessed portions) such that at least a portion of the second portion of the compressible layer is receivable within the recessed portions of the guide channel. In certain embodiments, wherein the second portion of the compressible layer is separable from the first portion of compressible layer, the second portion is slidable within the recessed portion of the guide channel and thus removable from the guide channel. As discussed herein the compressible layer may comprise one or more layers of material. For example, in some forms, the compressible layer may comprise a core material layer and one or more layers of a bolster support material. In accordance with some forms the core material comprises a relatively more rigid or stiff material than the bolster support material.

With reference to FIGS. 1-5, shown is various views of one embodiment of a tray 102 as provided by the present disclosure. In certain embodiments, tray 102 defines a guide channel 104 extending from an open end 120 to a closed end 122. In some forms, a guide channel wall 106 defines a first lateral wall 124, a second lateral wall 126, and/or the closed end 122 of the guide channel. In certain embodiments, the tray comprises a perimeter wall 130 extending along the outer edges of the tray. In some forms, the perimeter wall is contiguous with the guide channel wall. In accordance with some forms, the guide channel comprises a recessed portion 108 extending from at or near open end 120 along a length of the guide channel to a recessed portion end wall 114. In the illustrated embodiment, the recessed channels extend from the guide channel open end to the guide channel end wall at a point spaced from the guide channel end wall. It is envisioned that in some forms the guide channel may extend from the open end to the guide channel end wall. In accordance with some forms, tray 102 comprises a first tray component 150 and a second tray component 152. In some forms, receiving portion 154 is configured to receive a protrusion 156 to join the first and second tray components. In the illustrated embodiment, each of said first and second tray components is shown with two receiving portions on one side of the tray and two protrusions on the other side of the tray to facilitate bringing together and securing the tray components.

In certain embodiments, a tray may be configured to receive and secure a compressible layer configured to carry a bolster material. In some forms, the tray comprises a compressible layer attachment area 170. In certain embodiments, the compressible layer attachment area is formed by bringing together a first and second tray component. For example, one or more of the tray components may have molded area configured to receive one or more features of the compressible layer as disclosed herein. In some forms, the compressible layer attachment area is at or near the closed end of the guide channel.

Figure 2:
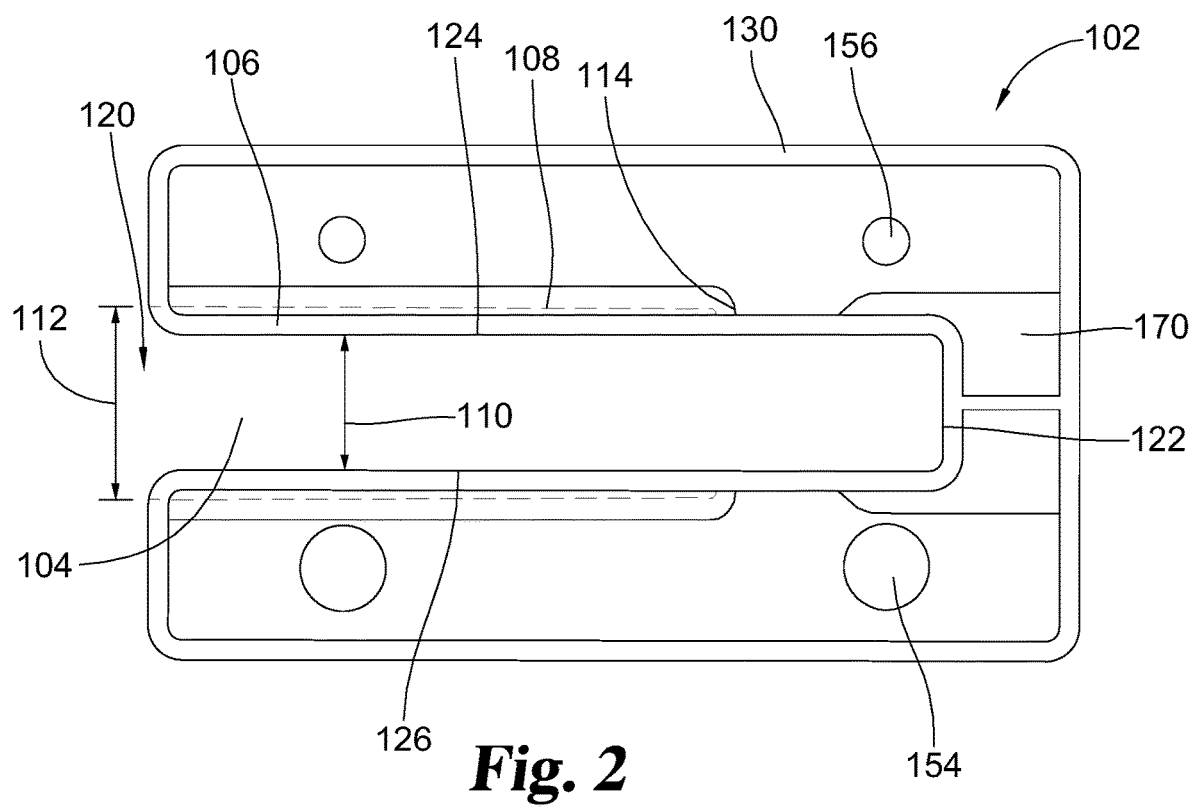
FIG. 2 is a top, plan view of one embodiment of a tray for loading a surgical bolster material onto a surgical stapling device as disclosed herein.
Figure 3:
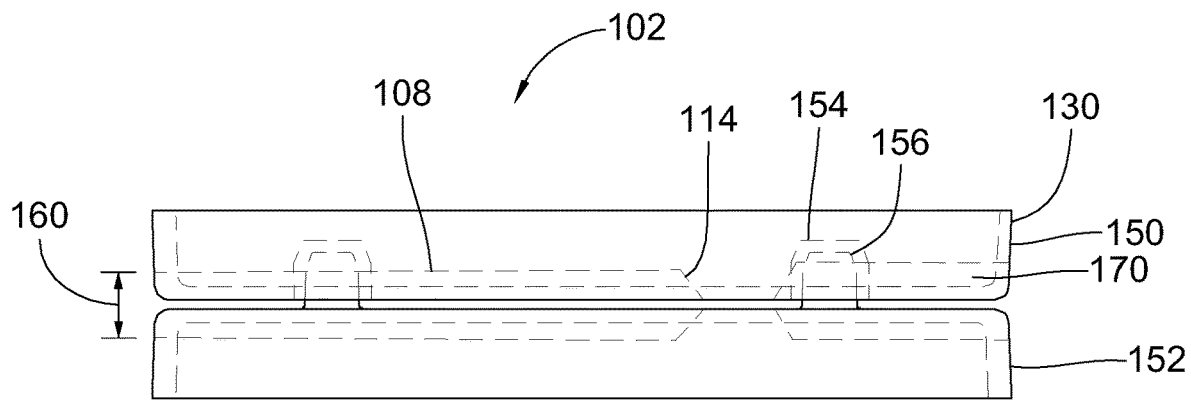
FIG. 3 is a side view of one embodiment of a tray for loading a surgical bolster material onto a surgical stapling device as disclosed herein.
Figure 4:
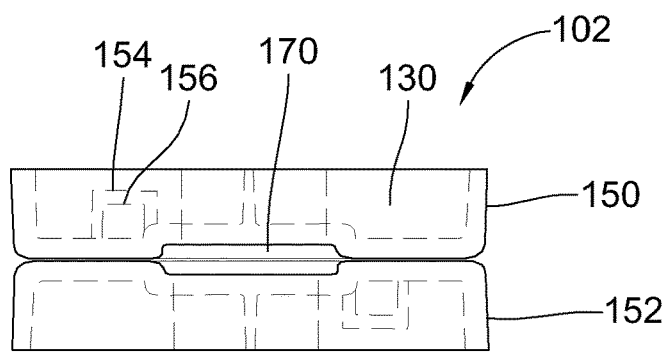
FIG. 4 is a rear end view of one embodiment of a tray for loading a surgical bolster material onto a surgical stapling device as disclosed herein.
Figure 5:
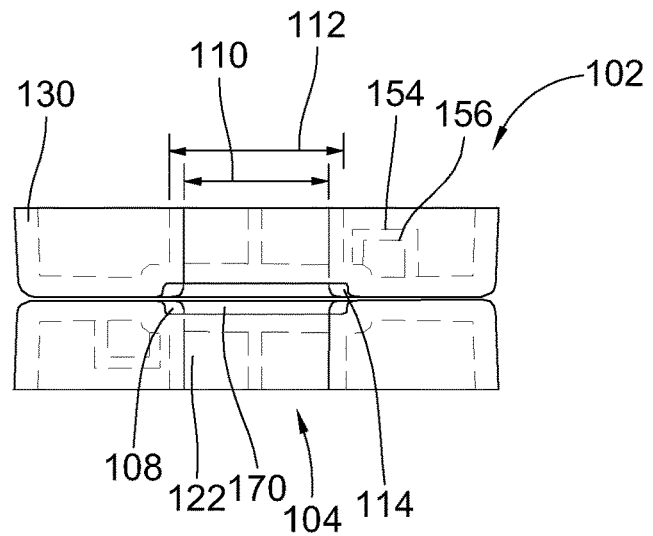
FIG. 5 is a front end view of one embodiment of a tray for loading a surgical bolster material onto a surgical stapling device as disclosed herein.

With particular reference to FIGS. 2, 3, and 5, as disclosed herein in accordance with some forms, guide channel may have a first channel width 110 between opposing faces of the channel wall outside of the recessed portions, and a second channel width 112 measured within the recessed portions. In some forms, the recessed portion has an opening width 160 measured along the plane of the channel wall over the opening formed by the recessed portion.

Figure 6A:
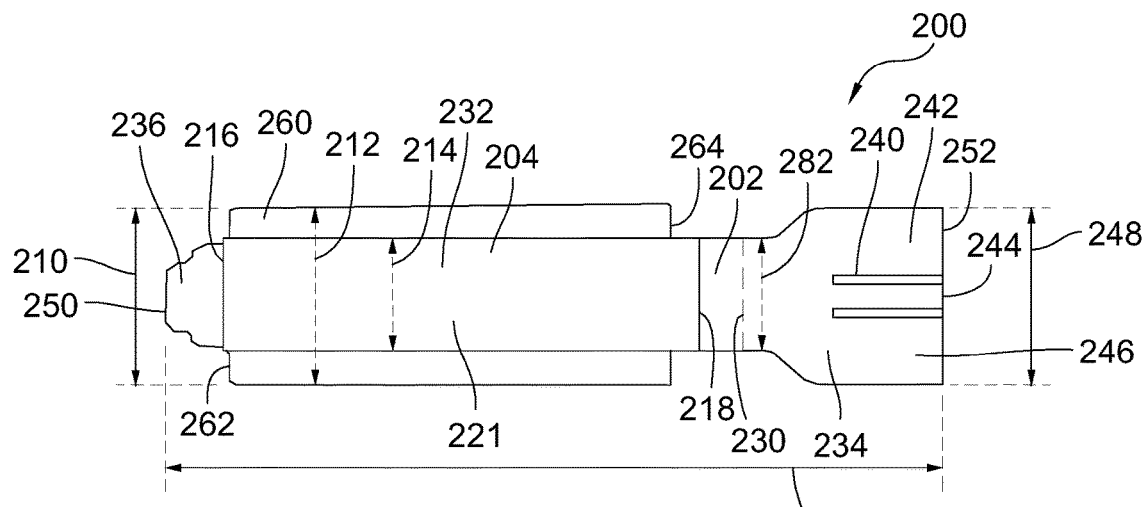
FIG. 6A is a top, plan view of one embodiment of a compressible layer as disclosed herein.
Figure 6B:
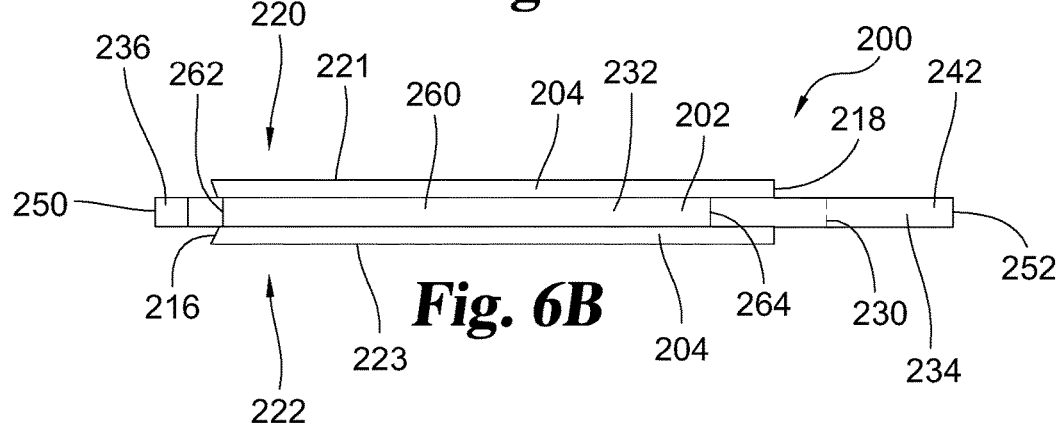
FIG. 6B is a side view of one embodiment of a compressible layer as disclosed herein.

With reference to FIGS. 6A and 6B, shown is one embodiment of a compressible layer 200 as provided by the present disclosure. In some forms, compressible layer 200 comprises a first portion 232 and a second portion 234. In certain embodiments, a detachable region 230 separates the first portion from the second portion. In some forms, the detachable region may comprise a weakened area to facilitate separation of the first portion from the second portion. For example in some forms, the weakened area comprises perforations.

In accordance with some forms, the compressible layer is configured to carry a bolster material as described herein. In certain embodiments, the compressible layer comprises a multilayer construct, comprising one or more layers of a bolster support material 204 carried by a core material 202. In some forms, the core material is relatively more rigid than the bolster support material. In certain embodiments, the bolster support material is relatively more compressible than the core material. In certain embodiments, the core material extends from a first end 250 to a second end 252. In some forms, the core material spans the entire length 270 of the compressible layer. In certain embodiments, the bolster support material extends from a first end 216 to a second end 218. In some forms, the first end of the bolster support material and the second end of the bolster support material are on the first portion of the compressible layer. In accordance with some forms, the first end of the core material extends beyond the first end of the bolster support material forming extended portion 236.

In certain embodiments, the compressible layer has a width 210 that is less than the second channel width 112 of a tray. In this way, the compressible layer is receivable within the guide channel with at least a portion of one or more guide members 260 received in a recessed portion. In accordance with some forms, guide member may comprise the core material and/or the bolster support material. In the illustrated embodiment, guide member 260 is formed by a portion of core member 260 having a width 212 larger than a width 214 of the overlying bolster support material. Guide member 260 may have a first end 262 and a second end 264. In some forms, the second end of guide member 260 is configured to contact the recessed portion end wall 114 of tray 102. In illustrated embodiment, the compressible layer comprises a guide member on each side to be slidably received in two recessed portions, in this way the compressible layer is supported within the guide channel along the lateral edges and by securement of the second portion as discussed herein.

In accordance with some forms, the second portion of the compressible layer is configured to secure the compressible layer within one or more tray members as described herein. In certain embodiments, the second portion may be configured to temporarily secure the bolster material to the compressible layer. In this way, the second portion 234 of compressible layer 200 may include one or more notches 240 configured to secure a portion of the bolster material as described herein. In the illustrated embodiment, notches 240 extend from the second end 252 of core material 202 forming central tab 244 and lateral tabs 246. It is also envisioned that one or more notches may be formed extending from the lateral edges of the compressible layer and/or into a central area of the compressible layer.

In certain embodiments, the second portion 234 of compressible layer 200 may have a flared shape. In the illustrated embodiment, second portion 234 forms flange 242 having a maximum width 248. As will be discussed herein, in some forms the second portion is configured to detach from the first portion and may be secured to one or more tray members. In this way in certain embodiments, compressible layer 200 may have a central portion 280 having a width 282 smaller than the maximum width 248 of second portion 234.

With reference to FIG. 6B, shown is a side view of one embodiment of a compressible layer as presently disclosed. The illustrated embodiment includes bolster support material 204 on a first side 220 and a second side 222 of the compressible layer. In certain embodiments, the bolster support material provides a first surface 221 and a second surface 223 for receiving a bolster material.

Figure 7:
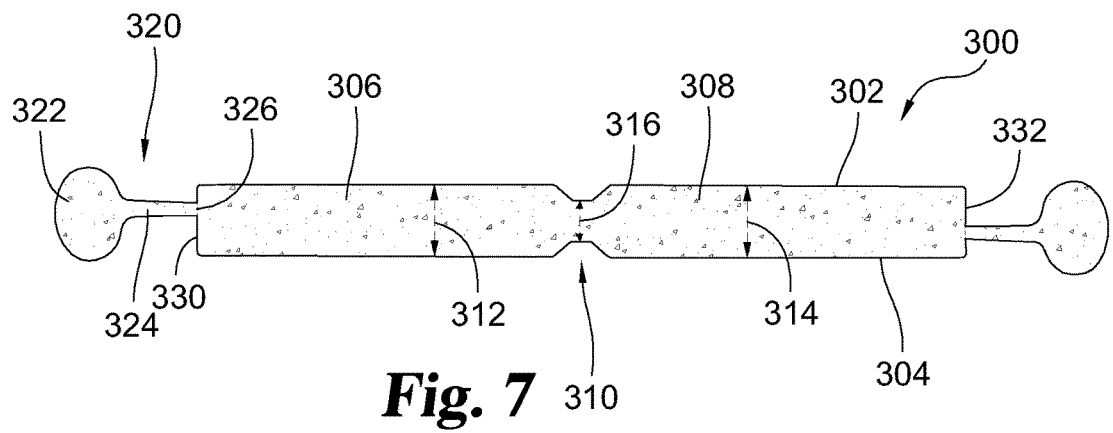
FIG. 7 is a top, plan view of one embodiment of a bolster material as disclosed herein.

FIG. 7 illustrates one embodiment of a bolster material as present disclosed. In the illustrated embodiment, bolster material 300 comprises a first sheet portion 306 and a second sheet portion 308. Bridge portion 310 connects first sheet portion to the second sheet portion. In some forms, bridge portion 310 has a bridge portion width 316 which is less than the width 312 of the first sheet portion and/or the width 314 of the second sheet portion. It is envisioned however, that bolster materials may be provided having a relatively consistent width from a first end to a second end. In certain embodiments, bolster material 300 has a first lateral edge 302 opposite a second lateral edge 304. In some forms, bolster material 300 includes an attachment member 320. Attachment member 320 may comprise any suitable configuration for attaching the bolster material to the compressible layer. In the illustrated embodiment, attachment member 320 comprises tab 322 and elongate portion 324. In accordance with some forms, attachment members may include a weakened area 326 to facilitate removal of attachment member from the remaining bolster material. Weakened area 326 may comprise any suitable configuration such as a perforation or tearable material. In the illustrated embodiment, bolster material 300 extends from a first end 330 to a second end 332 with attachment members 320 extending beyond said first end and said second end.

Figure 8:
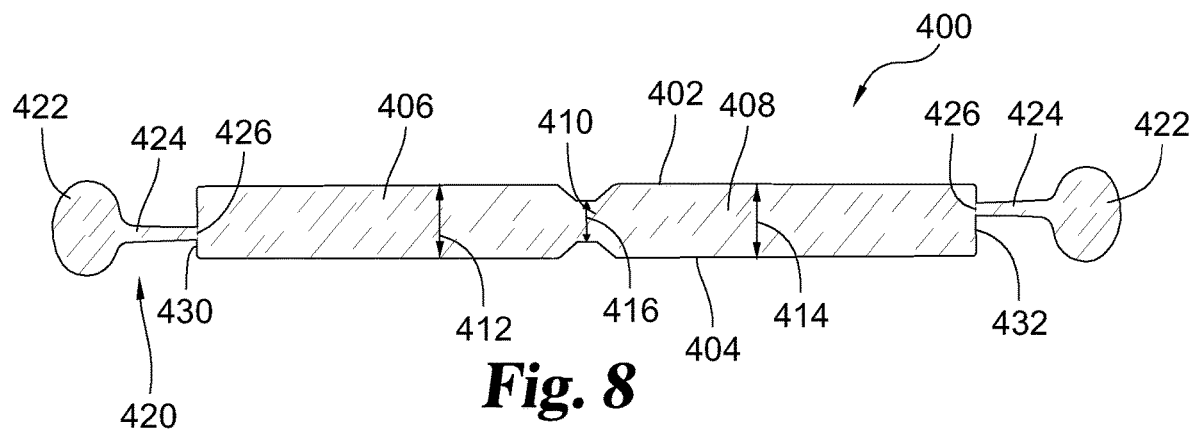
FIG. 8 is a top, plan view of one embodiment of a peelable protective cover as disclosed herein.

With reference to FIG. 8, in some forms the disclosed device includes a peelable protective cover. In accordance with some forms, the peelable protective cover has substantially the same shape as the bolster material so as to provide a protective cover for the underlining bolster material. Thus in the illustrated embodiment, protective cover 400 comprises a first sheet portion 406 and a second sheet portion 408. Bridge portion 410 connects first sheet portion to the second sheet portion. It is envisioned however, that peelable protective covers may be provided having a relatively consistent width from a first end to a second end. In some forms, bridge portion 410 has a bridge portion width 416 which is less than the width 412 of the first sheet portion and/or the width 414 of the second sheet portion. In certain embodiments, protective cover 400 has a first lateral edge 402 opposite a second lateral edge 404. In some forms, protective cover 400 includes an attachment member 420. Attachment member 420 may comprise any suitable configuration for attaching the protective cover to the compressible layer. In the illustrated embodiment, attachment member 420 comprises tab 422 and elongate portion 424. In accordance with some forms, attachment members may include a weakened area 426 to facilitate removal of attachment member from the remaining protective cover. Weakened area 426 may comprise any suitable configuration such as a perforation or tearable material. In the illustrated embodiment, protective cover 400 extends from a first end 430 to a second end 432 with attachment members 420 extending beyond said first end and said second end. In some forms, the peelable protective cover will have a first side having an anti-adhesive coating configured to prevent adhesion of the protective cover to the underlying bolster material and/or adhesive layer. In certain embodiments, the peelable protective cover may include an extended portion, for example the attachment members, to facilitate peeling of the cover from the bolster. In certain embodiments the peelable protective cover is releasably secured to the tray so as to prevent accidental dislodgement.

In certain embodiments, an adhesive layer may be used to facilitate temporary adhesion of the bolster material to the arm surfaces of a surgical stapling device. In accordance with some forms, an adhesive layer is formed on a first surface of the bolster material extending from the first lateral edge to the second lateral edge of the bolster material. In certain embodiments, the adhesive layer extends at least 90% preferably at least 95% of the width between the first lateral edge of the bolster material to the second lateral edge of the bolster material. In accordance with some forms, the adhesive layer extends essentially the entire width between the first lateral edge of the bolster material to the second lateral edge of the bolster material. In some forms, the bridge portion is free from adhesive. In certain embodiments, a portion of the bolster material along the lateral edge is free from adhesive. Any substance or means that increases the attachment of the bolster material to the arm surface can be used, so long as the attachment is not so permanent as to deleteriously interfere with release of the bolster material after the surgical stapler has been fired or otherwise actuated to insert the staple or staples. The substance can be inorganic, organic, natural or synthetic. In many cases, biocompatible surgical lubricants will suffice to improve this adhesion. Biocompatible adhesive materials, including pressure-sensitive adhesives, may also be used, including for example polyvinyl pyrrolidones, polyvinyl alcohols, polyvinyl acetates, vinyl acetate esters, starches, dextrins, acrylic resins, polyurethanes, styrene/butadiene radon copolymers, silicones, polyisobutylenes, polyisoprene polyvinyl ethyl ether and copolymers, blends or combinations thereof. In accordance with some forms the adhesive layer comprises and adhesive composition. In certain embodiments, the adhesive layer comprises an adhesive composition comprising a sugar alcohol component and one or more polysaccharides. In certain embodiments, the sugar alcohol component comprises sorbitol and/or maltitol. In certain embodiments, the polysaccharides of the adhesive composition comprise one or more of the following: chondroitin sulfate, and/or carboxymethylcellulose. In addition to the above, in some forms adhesive compositions for use with the present disclosure may also comprise sodium chloride. In certain embodiments, the adhesive composition comprises water, preferably high purity water. Thus in accordance with certain embodiments an adhesive composition may be formed by dissolving at least one sugar alcohol, and at least one polysaccharide in water. In other embodiments, the adhesive composition may comprise a sugar and/or a sugar alcohol and a polymer matrix. In certain embodiments, the sugar comprises fructose. In certain embodiments, the sugar alcohol comprises sorbitol. In certain embodiments, the polymer matrix comprises gelatin. In certain embodiments, a pre-applied adhesive can be covered with a peelable protective cover as described herein or similar material to protect the adhesive layer during shipping and handling. The protective cover can then be removed prior to use.

Figure 9A:
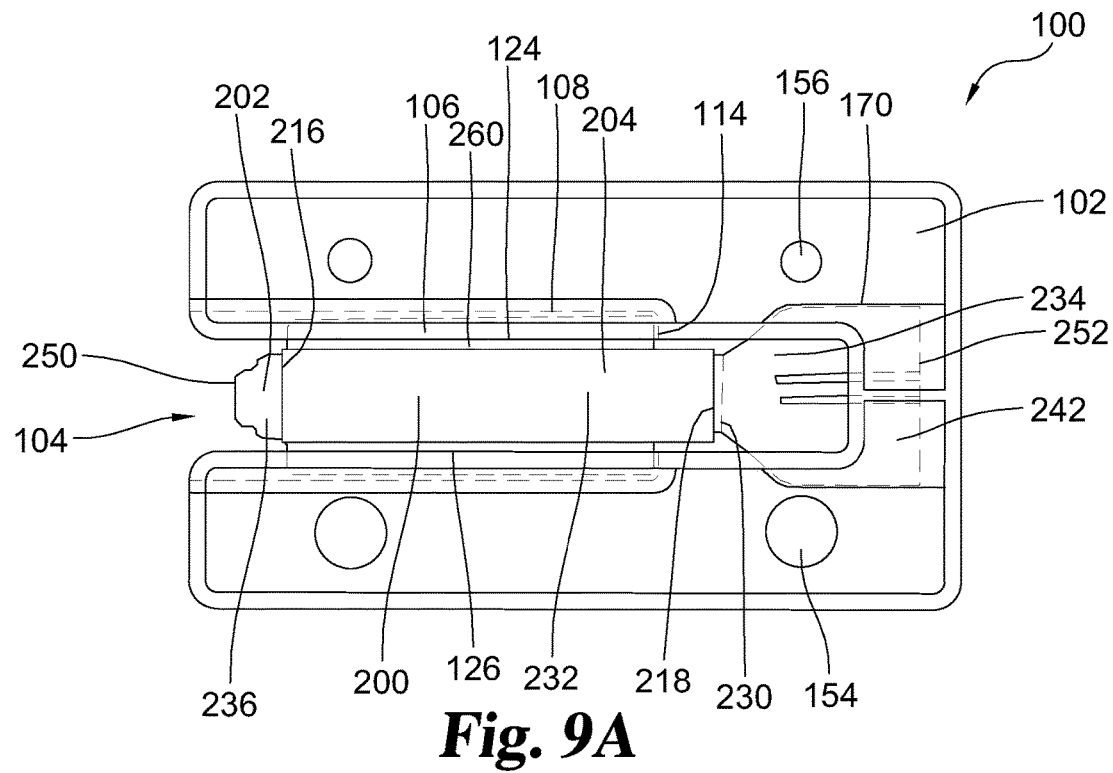
FIG. 9A is a top, plan view of one embodiment of a device for loading a surgical bolster material onto a surgical stapling device as disclosed herein.

FIG. 9a illustrates one embodiment of a device 100 comprising a tray 102 and a compressible layer 200 as described herein. In some forms, the second portion 234 of the compressible layer is securely received by the tray. In the illustrated embodiment, compressible layer attachment area 170 is configured to receive and secure flange 242 such that when the first portion 232 of the compressible layer is detached the second portion is retained in position within the tray. As disclosed herein, the compressible later may include one or more guide members 260 configured for receipt within recessed portions 108.

Figure 9B:
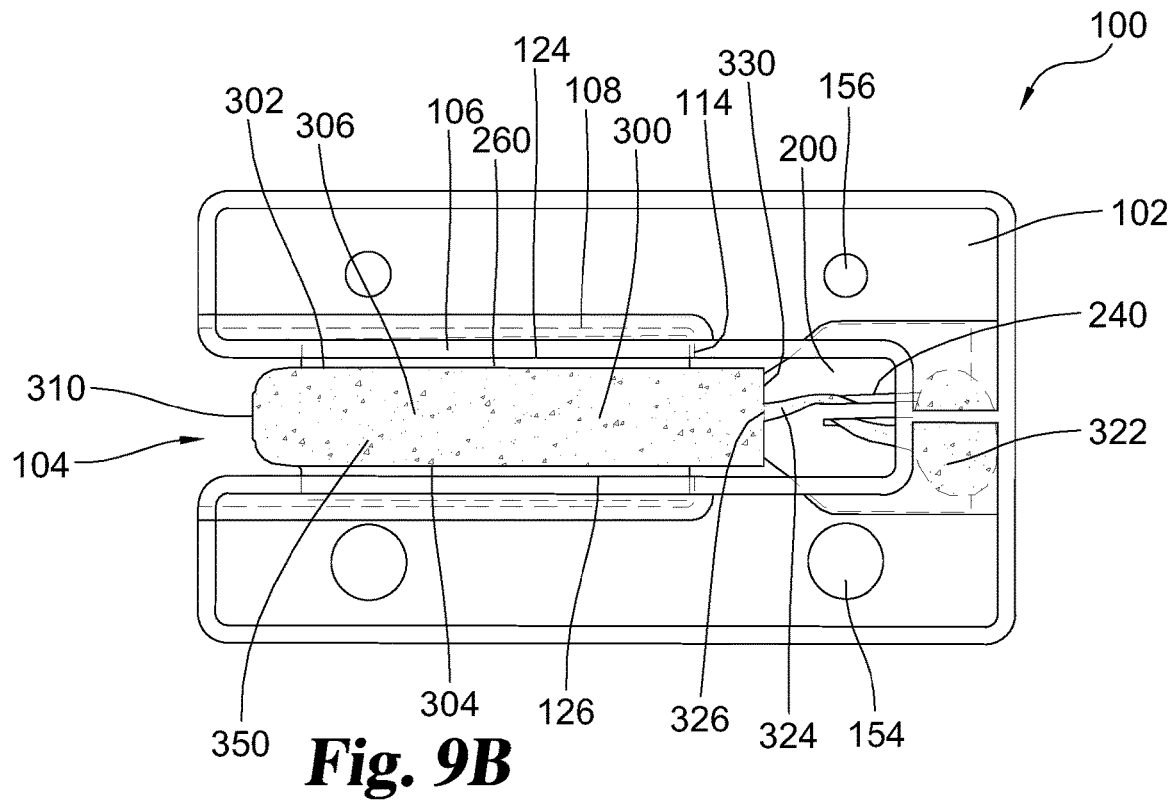
FIG. 9B is a top, plan view of one embodiment of a device for loading a surgical bolster material onto a surgical stapling device as disclosed herein.

FIG. 9B illustrates one embodiment of a device 100 comprising a tray, a compressible layer 200, and a bolster material 300. As disclosed herein, in certain embodiment a bolster material may be carried by a compressible layer. In the illustrated embodiment, bolster material 300 is carried by the compressible layer shown in more detail in FIG. 9A. Briefly, the bolster material may be secured to the compressible layer by securing one or more elongate portions 324 within one or more notches 240. In certain embodiments, the first and second sheet portions of the bolster material have a first side configured to fit against the compressible layer, the first side opposite a second side 350. In some forms, the second side may have an adhesive layer as described herein.

In certain embodiments, the bolster material is carried within a guide channel without compressing the bolster material. For example, as discussed herein the bolster material has a first lateral edge 302 and a second lateral edge 304, and the device disclosed is configured to receive the bolster material while retain the first and second lateral edges of the bolster material uncompressed by the tray.

Figure 9C:
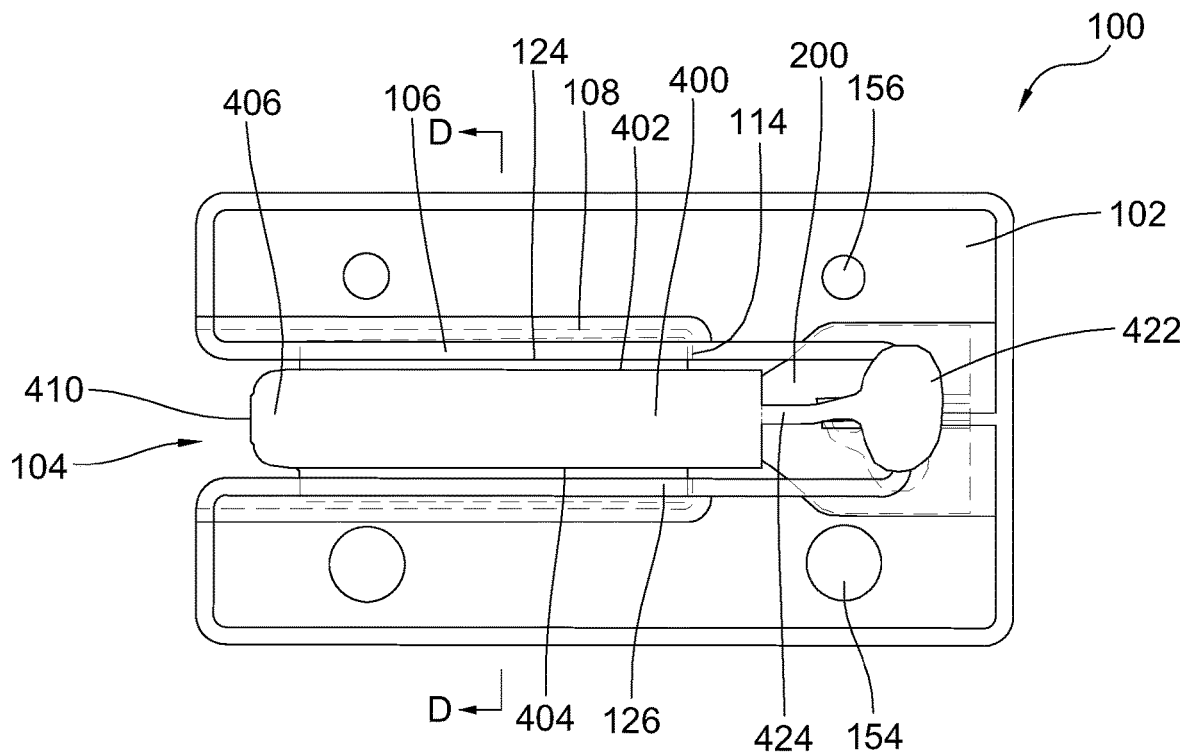
FIG. 9C is a top, plan view of one embodiment of a device for loading a surgical bolster material onto a surgical stapling device as disclosed herein.

FIG. 9C illustrates one embodiment of a device 100 comprising a tray, a compressible layer 200, a bolster material, and a peelable protective cover 400. As disclosed herein, in certain embodiments the device may include a peelable protective cover positioned over a bolster material.

With reference to FIGS. 10A, 10B, 10C, and 10G shown is one embodiment of a tray for loading a surgical bolster material onto a surgical device as presently disclosed. The illustrated embodiment shows a single tray component 150. In certain embodiments as discussed herein, the tray component is configured to pair with another substantially identical tray component to form a full tray. In some forms, the tray component comprises a guide channel wall portion 502 defining a portion of the guide channel 504. In the illustrated embodiment, the tray component comprises a receiving portion 154 configured to receive a corresponding protrusion 156 of a separate tray component. Thus as shown in the illustrated embodiments each tray component comprises one or more receiving portions and one or more protrusions. It is within the scope of the disclosure to provide tray components having only receiving portions and/or protrusions to facilitate attachment of the tray components. The tray component may comprise a first surface 500 configured to oppose and/or contact a similar surface on a separate tray component when attached to form a full tray. In certain embodiments, compressible layer attachment area 170 is formed as an indentation of the first surface. In certain embodiments, recessed portion(s) 108 is(are) formed by one or more indentations of the first surface along the guide channel wall portion.

Figure 10A:
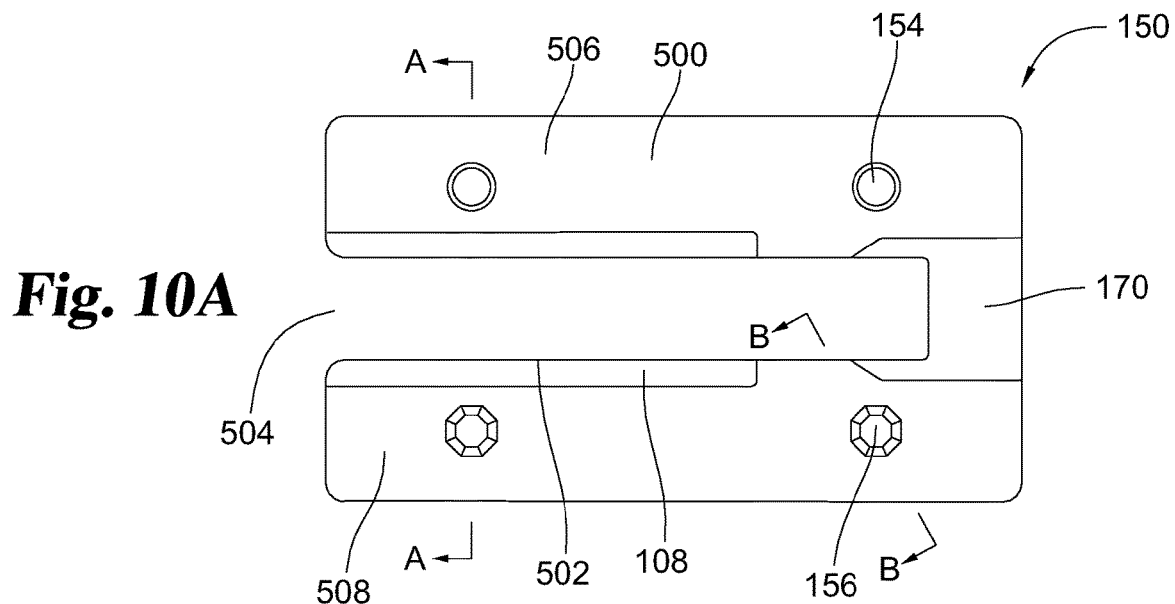
FIG. 10A is a top, plan view of one embodiment of a tray for loading a surgical bolster material onto a surgical stapling device as disclosed herein.
Figure 10B:
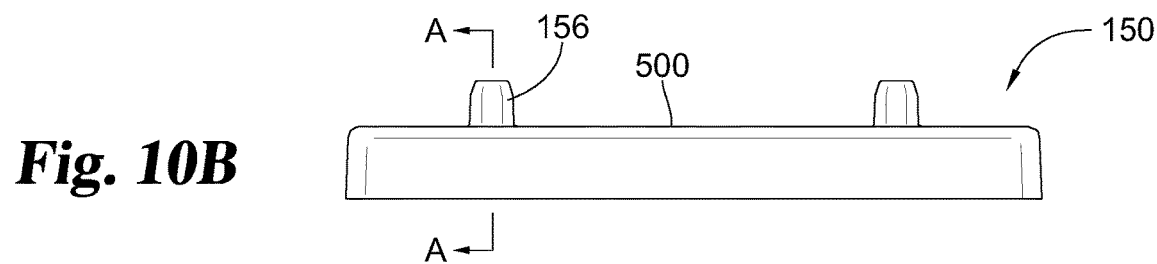
FIG. 10B is a side view of one embodiment of a tray for loading a surgical bolster material onto a surgical stapling device as disclosed herein.
Figure 10C:
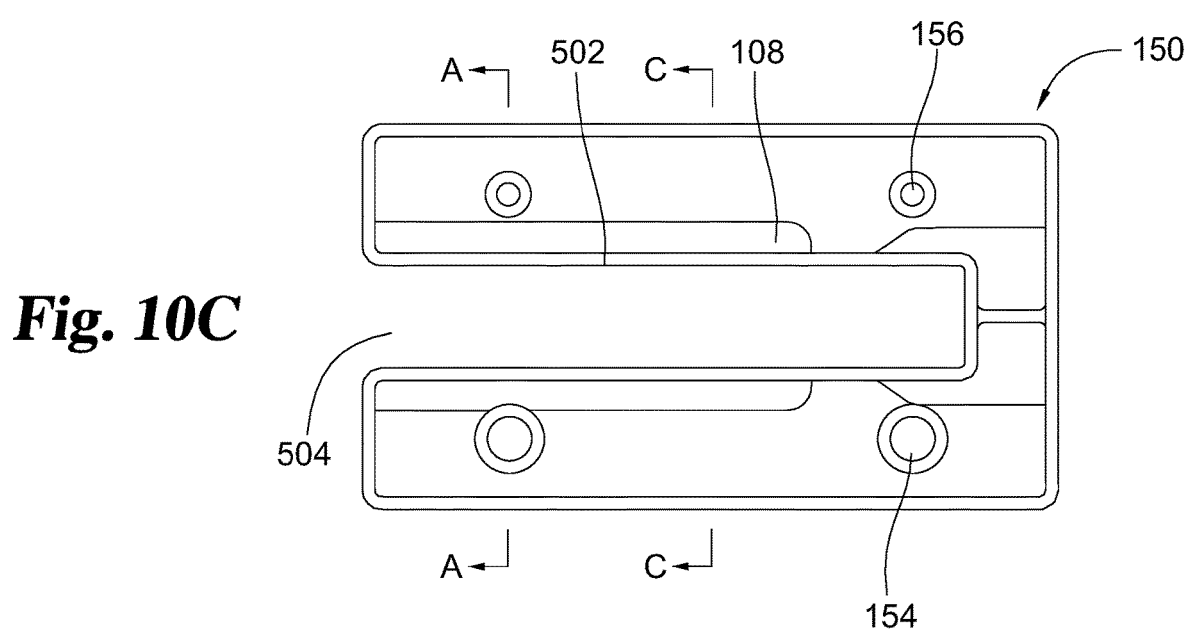
FIG. 10C is a bottom view of one embodiment of a tray for loading a surgical bolster material onto a surgical stapling device as disclosed herein.
Figure 10D:
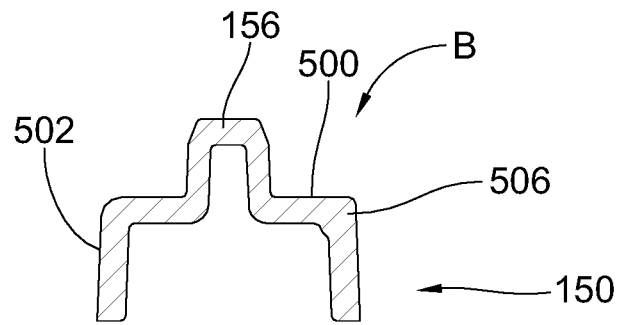
FIG. 10D is a cross-sectional view of section B (FIG. 10A).

FIG. 10D is a cross-sectional view of section B (FIG. 10A). The illustrated cross section B shows protrusion 156 extending from surface 500. In the illustrated embodiment, each structure is formed from a contiguous wall 506. In some forms, protrusion(s) may be formed from a solid material.

Figure 10E:
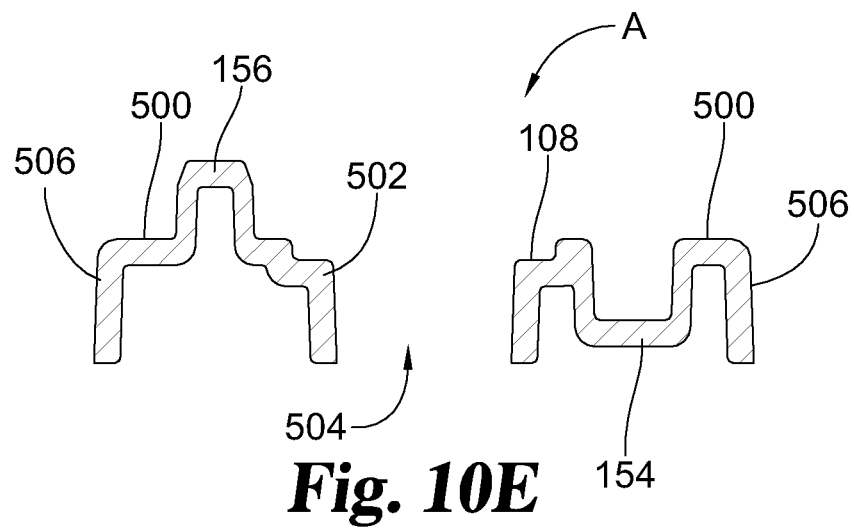
FIG. 10E is a cross-sectional view of section A (FIGS. 10A-C).

FIG. 10E is a cross-sectional view of section A. The illustrated cross section A shows protrusion 156 extending from surface 500, and receiving portion 154 extending from surface 500. In the illustrated embodiment, each structure is formed from a contiguous wall 506, although as noted above other variants are within the scope of the disclosure.

Figure 10F:
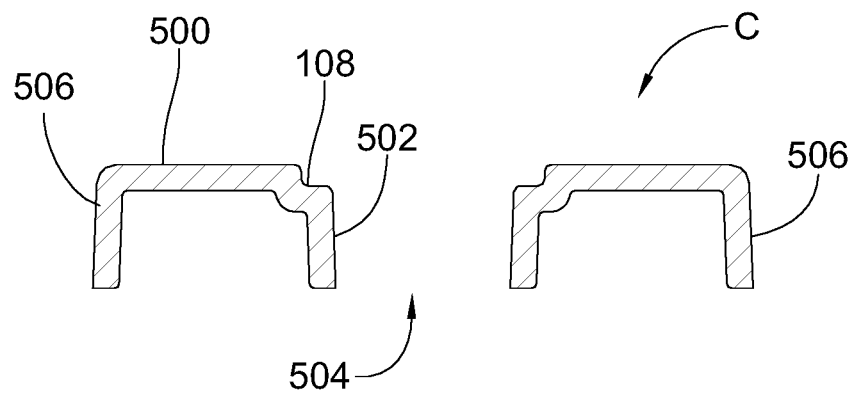
FIG. 10F is a cross-sectional view of section C (FIG. 10C).
Figure 10G:
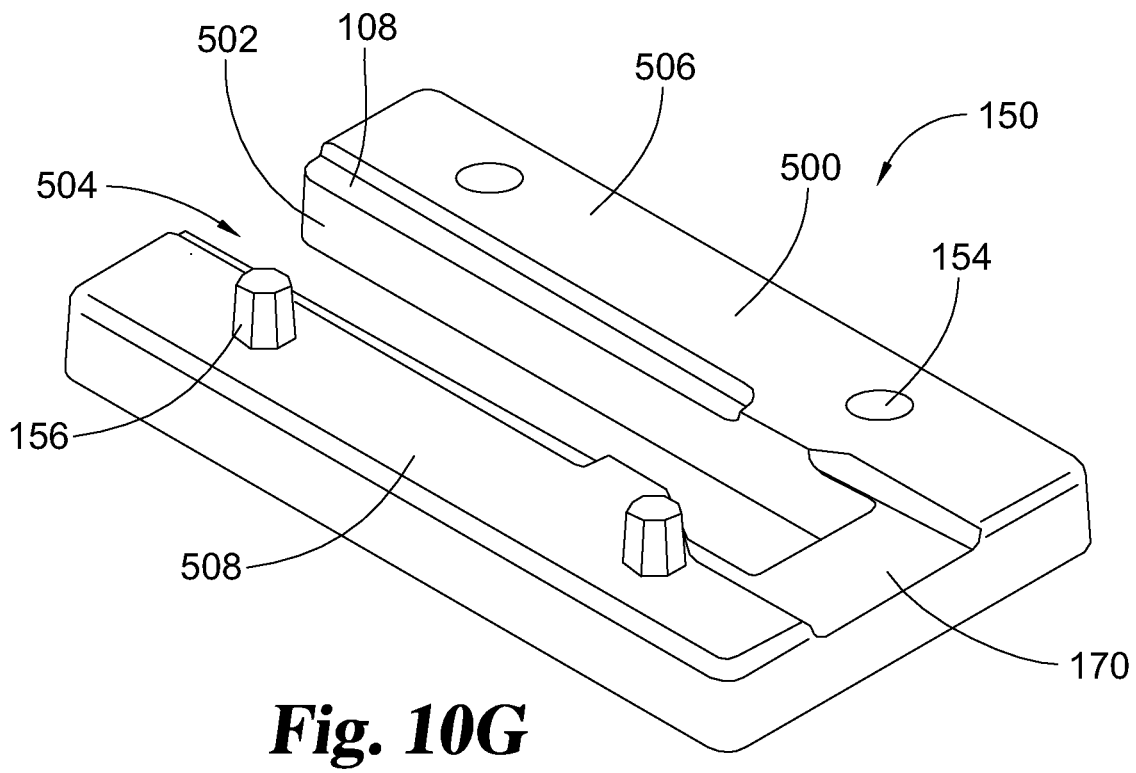
FIG. 10G is a perspective view of one embodiment of a tray for loading a surgical bolster material onto a surgical stapling device as disclosed herein.

FIG. 10F is a cross-sectional view of section C. The illustrated cross section C shows surface 500, and recessed portions(s) 108 extending from surface 500 along guide channel portion 502. In the illustrated embodiment, each structure is formed from a contiguous wall 506, although as noted above other variants are within the scope of the disclosure.

Figure 11:
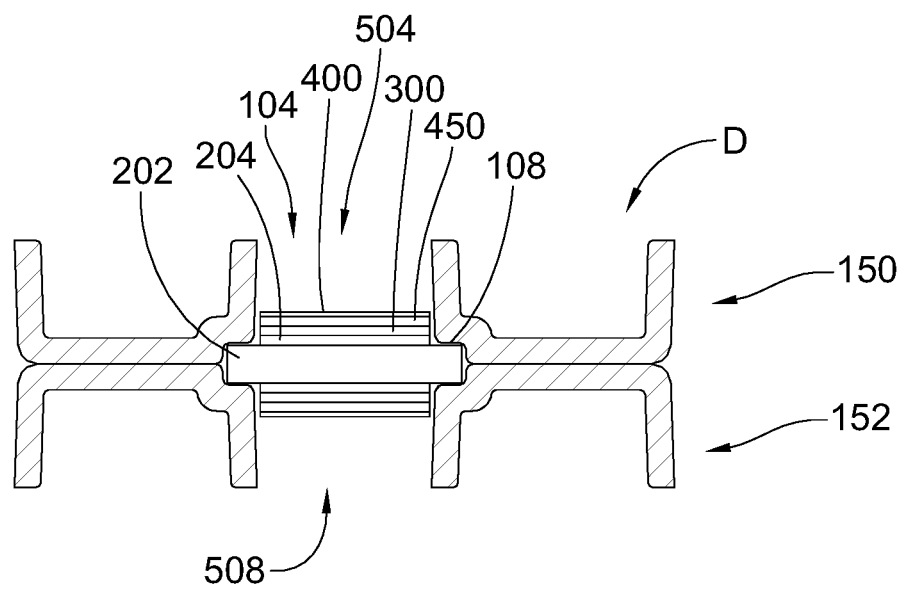
FIG. 11 is a cross sectional view of section D (FIG. 9C).

FIG. 11 is a cross-sectional view of section D (FIG. 9C). The illustrated cross section D shows a first tray component 150 defining a first guide channel portion 504 and a second tray component 152 defining a second guide channel portion 508. In the illustrated embodiment, a core material 202 is received within recessed portions 108 of guide channel 104.

The illustrated embodiment includes a layer of bolster support material 204 on opposing faces of the core material. The illustrated embodiment includes a bolster material 300 received on the bolster support material. In some forms, an adhesive layer 450 is present on an outer face (away from the core material) of the bolster material. Finally, a peelable protective cover 400 may be present over the adhesive layer and/or the bolster material.

In use, devices of the present disclosure are configured to provide a bolster material having at least a first lateral edge and a second lateral edge that are uncompressed by the tray. In accordance with some forms, an adhesive layer may be present on the bolster material. As discussed herein the adhesive layer may extend from the first lateral edge to the second lateral edge of the underlying bolster material. In certain embodiments, the adhesive layer has a first lateral edge and a second lateral edge that are uncompressed by the tray.

The present disclosure also provides for methods of loading a bolster material. In some forms, the disclosed methods comprise the step of providing a surgical stapling device having a receiving area for receipt of a bolster material, the receiving area including a first surface and a second surface. In certain embodiments, the disclosed methods may comprise the step of providing a loading device for loading a surgical bolster material onto the surgical stapling device. In some forms, the device may comprise any of the devices described herein. For example, in certain embodiments the device comprises one or more of the following: a tray defining a guide channel for receipt of a bolster material to be applied to the surgical stapling device, a compressible layer having a first portion compressed by the tray, and a second portion extending into the guide channel, a bolster material carried by the compressible layer, an adhesive layer on the bolster material and configured to adhere the bolster material to the stapler, and/or a peelable protective cover over the adhesive layer, the peelable protective cover peelable from the adhesive layer while the compressible layer and the bolster material are received in the tray with the bolster material in the guide channel. In some forms, the disclosed methods include the step of removing the peelable protective cover, while the compressible layer and the bolster material are received in the tray with the bolster material in the guide channel. In certain embodiments, the disclosed methods include the step of contacting the receiving area with the adhesive layer to adhere the bolster material to the surgical stapling device.

Turning now to a discussion of the bolster material, any suitable biocompatible material can be used in the broader aspects of the invention. Reconstituted or naturally-derived collagenous bolster materials are desirable, especially collagenous extracellular matrix materials, such as submucosa, renal capsule membrane, dura mater, pericardium, serosa, peritoneum, dermal collagen, or basement membrane. The preferred bolster materials of the invention will include submucosa, such as submucosa derived from a warm-blooded vertebrate. Mammalian submucosa materials retaining substantially their native cross-linking are preferred, although additionally crosslinked materials may also be used. In particular, extracellular matrix materials derived from animals raised for meat or other product production, e.g. pigs, cattle or sheep, will be advantageous. Porcine submucosa provides a particularly preferred material for use in the present invention.

The submucosa can be derived from any suitable organ or other biological structure, including for example submucosa derived from the alimentary, respiratory, intestinal, urinary or genital tracts of warm-blooded vertebrates. Submucosa useful in the present invention can be obtained by harvesting such tissue sources and delaminating the submucosa from smooth muscle layers, mucosal layers, and/or other layers occurring in the tissue source. For additional information as to submucosa useful in the present invention, and its isolation and treatment, reference can be made, for example, to U.S. Pat. Nos. 4,902,508, 5,554,389, 5,993,844, 6,206,931, and 6,099,567.

When a submucosa or other ECM material having differing characteristic sides is used in the invention, it can be oriented upon the medical device with a specified side directed outward for contact with the arm(s) of the surgical fastening device. For example, in the case of small intestinal submucosa, the material may be oriented with either the luminal or abluminal side facing outwardly for contact with the arm(s) of the surgical fastening device.

As prepared, an extracellular matrix (ECM) material for use in the present invention may optionally retain growth factors or other bioactive components native to the source tissue. For example, the matrix material may include one or more growth factors such as basic fibroblast growth factor (FGF-2), transforming growth factor beta (TGF-beta), epidermal growth factor (EGF), and/or platelet derived growth factor (PDGF). As well, submucosa or other ECM material of the invention may include other biological materials such as heparin, heparin sulfate, hyaluronic acid, fibronectin and the like. Thus, generally speaking, the ECM material may include a bioactive component that induces, directly or indirectly, a cellular response such as a change in cell morphology, proliferation, growth, protein or gene expression. Further, in addition or as an alternative to the inclusion of such native bioactive components, non-native bioactive components such as those synthetically produced by recombinant technology or other methods, may be incorporated into the ECM material.

ECM material used in the invention is preferably highly purified, for example, as described in U.S. Pat. No. 6,206,931. Thus, preferred material will exhibit an endotoxin level of less than about 12 endotoxin units (EU) per gram, more preferably less than about 5 EU per gram, and most preferably less than about 1 EU per gram. As additional preferences, the ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plate forming units (PFU) per gram, more preferably less than about 5 PFU per gram. These and additional properties of submucosa tissue taught in U.S. Pat. No. 6,206,931 may be characteristic of the ECM material used in the present invention.

Other implantable materials that may be employed as staple bolster materials in the present invention include non-bioresorbable or bioresorbable synthetic polymer materials such as polytetrofluroethylene (PTFE, e.g. GORE-TEX material), nylon, polypropylene, polyurethane, silicone, DACRON polymer, polyglycolic acid (PGA), polylactic acid (PLA), polycaprolactone, or others.

When a collagenous material is used as a staple bolster material in the invention, it may be desirable to bond areas of the collagenous material to one another, for example in securing the bolster material around all or a portion of an associated applicator element. Glues or other bonding agents may be used for this purpose, as discussed above. In addition or alternatively, collagenous material layers can be dehydrothermally bonded to one another, for example by drying the layers in contact with one another, e.g. under compression. The drying operation can, for example, occur in a lyophilization (freeze drying) or vacuum pressing process.

In certain embodiments of the invention, the staple bolster material will have a thickness in the range of about 50 to about 1000 microns, more preferably about 100 to 600 microns, and most preferably about 100 to about 350 microns. The staple bolster material will desirably provide sufficient strength to effectively reinforce the staple(s), for example exhibiting a suture retention strength in the range of about 100 to about 1000 gram force, e.g. typically in the range of about 200 to about 600 gram force, each of these based upon 5-0 Prolene suture and a bite depth of 2 mm. If necessary or desired, a multilaminate staple bolster material can be used. For example, a plurality of (i.e. two or more) layers of collagenous material, for example submucosa-containing or other ECM material, can be bonded together to form a multilaminate structure useful as a staple bolster material. Illustratively, two, three, four, five, six, seven, or eight or more collagenous layers containing submucosal or other collagenous ECM materials can be bonded together to provide a multilaminate collagenous bolster material. In certain embodiments, two to six collagenous, submucosa-containing layers isolated from intestinal tissue of a warm-blooded vertebrate, particularly small intestinal tissue, are bonded together to provide the staple bolster material. Porcine-derived small intestinal tissue is preferred for this purpose. The layers of collagenous tissue can be bonded together in any suitable fashion, including dehydrothermal bonding under heated, non-heated or lyophilization conditions, using adhesives, glues or other bonding agents, cross-linking with chemical agents or radiation (including UV radiation), or any combination of these with each other or other suitable methods.

The medical devices of the present invention can be used to facilitate a variety of surgical procedures. Such procedures include but are not limited to various lung resection procedures (e.g., blebectomies, lobectomoies, bullectomies, wedge resections, and lung reduction procedures, such as those used to treat symptoms of emphysema); treatment of soft tissue injuries and defects (e.g., abdominal or thoracic wall procedures, gastro-intestinal procedures), and as a tool in a variety of other surgical procedures (e.g., reproductive organ repair procedures, etc.). In this regard, the medical devices of the invention may be used in conjunction with operations on both humans and animals. Likewise, the medical devices of the invention may be used with either anastomotic staplers or non-anastomotic staplers, and may be adapted, sized and shaped in a variety of ways to accommodate given stapler devices.

The medical devices of the invention can be provided in sterile packaging suitable for medical products. Sterilization may be achieved, for example, by irradiation, ethylene oxide gas, or any other suitable sterilization technique, and the materials and other properties of the medical packaging will be selected accordingly. In certain embodiments, the medical device is package in such a way so as to control the humidity within the sterile package. In some forms, the package includes a humidity control device, for example a device containing a desiccant such as a packet or card. In accordance with certain inventive variants, the sterile package includes a pocket configured to contain a humidity control device. In some forms, the medical packaging comprises a vapor impermeable material, for example a metallic foil (e.g. aluminum), or a polymeric material. In certain embodiments, the medical packaging will be selected to maintain a desired humidity level within a sealed package containing a medical device as described herein. In some forms, the medical package is configured to maintain a humidity level of about 45% to about 75% relative humidity within the sealed medical package containing a medical device as described herein, preferably about 50% to about 65% relative humidity within the sealed medical package containing a medical device as described herein, even more preferably about 55% to about 60% relative humidity within the sealed medical package containing a medical device as described herein. In certain embodiment, the medial packaging is selected to maintain a relative humidity of about 58% within the sealed medical package containing a medical device as described herein.

Figure 12:
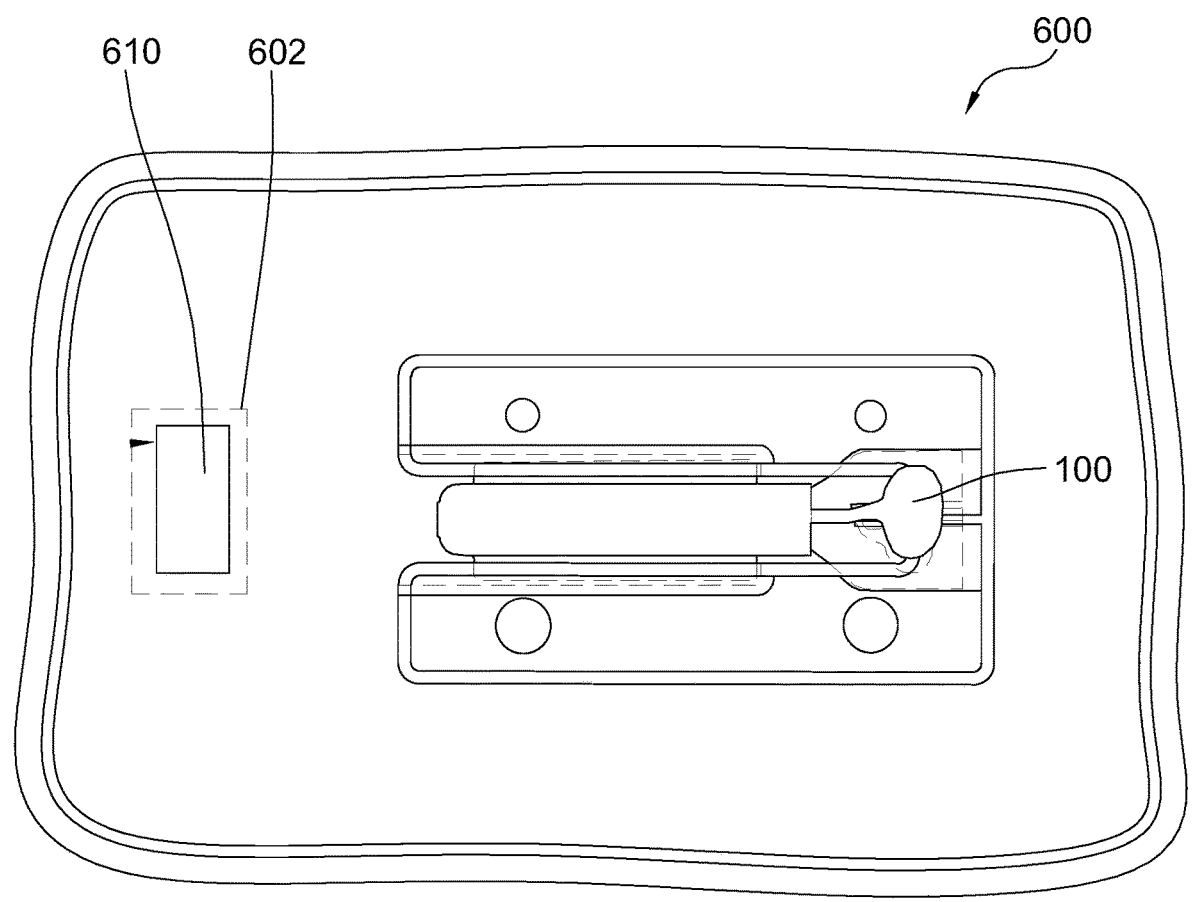
FIG. 12 is a top, plan view of one embodiment of a device for loading a surgical bolster material onto a surgical stapling device as disclosed herein within a sterile medical package.

With reference to FIG. 12, FIG. 12 illustrates one embodiment of a device for loading a surgical bolster material onto a surgical stapling device as disclosed herein within a sterile medical package. In the illustrated embodiment, device 100 is contained within sterile package 600. Sterile package 600 includes pocket 602 configured to contain humidity control device 610.

The following specific Examples are provided to promote a further understanding of certain aspects of the present disclosure. It will be understood that these Examples are illustrative, and not limiting, in character.

Example 1

Preparation of Adhesive Composition

Adhesive compositions were prepared having the formulations listed in Table 1.

TABLE 1

Formulation details for adhesive compositions, Key:
CS—Chondroitin Sulfate, CMC—Carboxymethyl cellulose,
HPW—High Purity Water, PASA—Poly(aspartic acid),
PAA—Poly(acrylic acid)

| Formulation ID | Components | Component Ratio |
|---|---|---|
| 1023A | CS:CMC:Sorbitol:HPW | 3:1:30:50 |
| 1023B | CS:CMC:Sorbitol:HPW | 3:1:30:33.3 |
| 1023C | CS:CMC:Sorbitol:HPW | 6:1:30:50 |
| 1023D | CS:CMC:Sorbitol:HPW | 3:1:50:50 |
| 1023E | CS:CMC:Sorbitol:HPW | 1:1:10:16.7 |
| 1023EG | CS:CMC:Glycerine:Sorbitol:HPW | 1:1:0.83:10:16.7 |
| 1023F | PASA:Sorbitol:HPW | 1:5:10 |
| 1023G | PAA:Sorbitol:HPW | 1:5:10 |
| 1023H | CS:CMC:Sorbitol:HPW | 3:1:15:35 |
| 1023I | CS:CMC:Sorbitol:HPW | 1:1:15:17.5 |
| 1023IG | CS:CMC:Sorbitol:Glycerine:HPW | 1:1:0.87:15:17.5 |
| Maltitol | CS:CMC:Sorbitol:Maltitol:NaCl:HPW | 1:1:10:3:1.7:13.3 |

Dry components of the adhesive compositions were weighed out, sifted together, and added to mixed liquid components (HPW or HPW and glycerin). Solutions were then dissolved on a shaker at 60 RPM for at least 4 hours.

Example 2

Preparation of Bolster Materials

Each of the formulations prepared according to Example 1 were coated onto 4-layer lyophilized SIS sheets using a 0.05 inch wire-wound rod. The coated sheets dried overnight at ambient humidity, then placed in a humidified container to equilibrate overnight. After equilibration, a release liner was applied to the coated surface of each sheet. Sheets were then laser cut to the desired shape using an Epilog laser cutter. Laser cut devices were packages in foil pouches with a 2-way humidifier packet (either 49% or 58%) to maintain humidity within the pouch. Some of the devices were sterilized with electron beam sterilization (dose: 26.0-39.3 kGy).

Listing of Certain Embodiments

The following provides an enumerated listing of some of the embodiments disclosed herein. It will be understood that this listing is non-limiting, and that individual features or combinations of features (e.g. 2, 3 or 4 features) as described in the Detailed Description above can be incorporated with the below-listed Embodiments to provide additional disclosed embodiments herein.

1. A device for loading a surgical bolster material onto a surgical stapling device, said device comprising:
    a tray defining a guide channel for receipt of a bolster material to be applied to the surgical stapling device;
    a compressible layer having a compressed portion compressed by said tray, and an elongate detachable portion extending into said guide channel, said detachable portion detachable from said compressed portion, said elongate detachable portion comprising a first lateral edge opposite a second lateral edge, and wherein said first lateral edge and said second lateral edge are uncompressed by said tray;
    a bolster material carried by said compressible layer, wherein said bolster material comprises a first lateral edge and a second lateral edge opposite said first lateral edge, and wherein said first lateral edge of said bolster material and said second lateral edge of said bolster material are uncompressed by said tray;
    an adhesive layer on said bolster material and configured to adhere said bolster material to the stapler; and
    a peelable protective cover over said adhesive layer, said peelable protective cover peelable from said adhesive layer while said compressible layer and said bolster material are received in said tray with said bolster material in said guide channel
2. The device of embodiment 1, wherein said adhesive layer comprises a first lateral edge and a second lateral edge, and wherein said first lateral edge of said adhesive layer and said second lateral edge of said adhesive layer are uncompressed by said tray.
3. The device of any one of the preceding embodiments, wherein said guide channel is defined by a channel wall, wherein said channel wall includes one or more recessed portions, said guide channel having a first channel width between opposing faces of said channel wall outside of said recessed portions, a second channel width between opposing portions of said channel wall within said recessed portions, and wherein said second channel width is greater than said first channel width.
4. The device of embodiment 3, wherein said detachable portion has a width between said first lateral edge and said second lateral edge, and wherein said detachable portion width is less than said second channel width.
5. The device of embodiment 4, wherein said detachable portion width is greater than said first channel width, such that a portion of said detachable portion rests within said one or more recessed portions.
6. The device of any one of embodiments 3 to 5, wherein said bolster material has a width between said first lateral edge and said second lateral edge, and wherein said width of said bolster material is equal to or less than said first channel width.
7. The device of embodiment 6, wherein said bolster material has a width between said first lateral edge and said second lateral edge, and wherein said width of said bolster material is less than said first channel width.
8. The device of any one of the preceding embodiments, wherein said compressible layer comprises a multilayer construct, comprising one or more layers of a bolster support material carried by a core material.
9. The device of embodiment 8, wherein said core material has a maximum width greater than a maximum width for said bolster support material.
10. The device of any one of the preceding embodiments, wherein said bolster material comprises:
    a first sheet portion carried on a first side of said compressible layer;
    a second sheet portion carried by a second side of said compressible layer; and
    a bridge portion connecting said first sheet portion to said second sheet portion.
11. The device of any one of the preceding embodiments, wherein said compressible layer comprises a weakened region between said compressed portion and said detachable portion.
12. The device of any one of the preceding embodiments, wherein said bolster material comprises one or more attachment members configured to releasably secure said bolster material to said compressible layer.
13. The device of embodiment 12, wherein said compressed portion of said compressible layer comprises one or more notches configured to receive and secure said attachment members of said bolster material.
14. The device of embodiment 13, wherein said attachment members of said bolster material are compressed by said tray.
15. The device of any one of embodiments 12 through 14, wherein said attachment members of said bolster material are detachable from a region of the bolster material positioned in said channel.
16. The device of any one of the preceding embodiments, wherein a portion of said bolster material and said detachable portion of said compressible layer are detachable from the tray.
17. The device of any one of the preceding embodiments, wherein said bolster material comprises a collagenous material.
18. The device of any one of embodiments 1 through 16, wherein said bolster comprises a bioresorbable synthetic polymer.
19. The device of any one of the preceding embodiments, wherein said peelable protective cover comprises an extended portion configured to facilitate removal of the protective cover from the bolster material.
20. A device for loading a surgical bolster material onto a surgical stapling device, said device comprising:
    a tray defining a guide channel for receipt of a bolster material to be applied to the surgical stapling device;
    a compressible layer having a secured portion secured by said tray, and a detachable portion extending into said guide channel, said detachable portion detachable from said secured portion;
    a bolster material carried by said compressible layer, wherein said bolster material comprises a first lateral edge and a second lateral edge;

an adhesive layer on said bolster material and configured to adhere said bolster material to the stapler; wherein said adhesive layer extends at least essentially the entire width between said first lateral edge of said bolster material and said second lateral edge of said bolster material; and a peelable protective cover over said adhesive layer, said peelable protective cover peelable from said adhesive layer while said compressible layer and said bolster material are received in said tray with said bolster material in said guide channel 21. The device of embodiment 20, wherein said adhesive layer comprises a first lateral edge and a second lateral edge, and wherein said first lateral edge of said adhesive layer and said second lateral edge of said adhesive layer are uncompressed by said tray.

22. The device of any one of embodiments 20 or 21, wherein said guide channel is defined by a channel wall, wherein said channel wall includes one or more recessed portions, said guide channel having a first channel width between opposing faces of said channel wall outside of said recessed portions, a second channel width between opposing portions of said channel wall within said recessed portions, and wherein said second channel width is greater than said first channel width.

23. The device of embodiment 22, wherein said detachable portion of said compressible layer has a width between a first elongate lateral edge and a second elongate lateral edge, and wherein said compressible layer width is less than said second channel width.

24. The device of embodiment 23, wherein said detachable portion width is greater than said first channel width, such that a portion of said compressible layer rests within said one or more recessed portions.

25. The device of any one of embodiments 22 to 24, wherein said bolster material has a width between said first lateral edge and said second lateral edge, and wherein said width of said bolster material is equal to or less than said first channel width.

26. The device of embodiment 25, wherein said bolster material has a width between said first lateral edge and said second lateral edge, and wherein said width of said bolster material is less than said first channel width.

27. The device of any one of embodiments 20 to 26, wherein said compressible layer comprises a multilayer construct, comprising one or more layers of a bolster support material carried by a core material.

28. The device of embodiment 27, wherein said core material has a maximum width greater than a maximum width for said bolster support material.

29. The device of any one of embodiments 20 to 28, wherein said bolster material comprises:
a first sheet portion carried on a first side of said compressible layer;
a second sheet portion carried by a second side of said compressible layer; and
a bridge portion connecting said first sheet portion to said second sheet portion.

30. The device of any one of embodiments 20 to 29, wherein said compressible layer comprises a weakened area between said detachable portion and said secured portion.

31. The device of any one of embodiments 20 to 30, wherein said bolster material comprises one or more attachment members configured to releasably secure said bolster material to said compressible layer.

32. The device of embodiment 31, wherein said secured portion of said compressible layer comprises one or more notches configured to receive and secure said attachment members of said bolster material.

33. The device of any one of embodiments 31 or 32, wherein said attachment members of said bolster material are detachable from a region of the bolster material positioned in said guide channel.

34. The device of any one of embodiments 20 to 33, wherein a portion of said bolster material and said detachable portion of said compressible layer are detachable from the tray.

35. The device of any one of embodiments 20 through 33, wherein said bolster material comprises a collagenous material.

36. The device of any one of embodiments 20 to 33, wherein said bolster comprises a bioresorbable synthetic polymer.

37. A device for loading a surgical bolster material onto a surgical stapling device, said device comprising:
a tray defining a guide channel for receipt of a bolster material to be applied to the surgical stapling device;
a compressible layer having a compressed portion compressed by said tray, a detachable portion extending into said guide channel, wherein said detachable portion is detachable from said compressed portion;
a bolster material carried by said compressible layer;
an adhesive layer on said bolster material and configured to adhere said bolster material to the stapler; and
a peelable protective cover over said adhesive layer, said peelable protective cover peelable from said adhesive layer while said compressible layer and said bolster material are received in said tray with said bolster material in said guide channel.

38. The device of embodiment 37, wherein said bolster material comprises a first lateral edge and a second lateral edge, and wherein said first lateral edge of said bolster material and said second lateral edge of said bolster material are uncompressed by said tray;

39. The device of any one of embodiments 37 or 38, wherein said compressible layer comprises a weakened region between said compressed portion and said detachable portion.

40. The device of any one of embodiments 37 to 39, wherein said adhesive layer comprises a first lateral edge and a second lateral edge, and wherein said first lateral edge of said adhesive layer and said second lateral edge of said adhesive layer are uncompressed by said tray.

41. The device of any one of embodiments 37 to 40, wherein said guide channel is defined by a channel wall, wherein said channel wall includes one or more recessed portions, said guide channel having a first channel width between opposing faces of said channel wall outside of said recessed portions, a second channel width between opposing portions of said channel wall within said recessed portions, and wherein said second channel width is greater than said first channel width.

42. The device of embodiment 41, wherein said detachable portion of said compressible layer has a width between a first elongate lateral edge and a second elongate lateral edge, and wherein said width of said detachable portion is less than said second channel width.

43. The device of embodiment 42, wherein said width of said detachable portion is greater than said first channel width, such that a portion of said detachable portion rests within said one or more recessed portions.

44. The device of any one of embodiments 41 to 43, wherein said bolster material has a width between a first lateral edge and a second lateral edge, and wherein said width of said bolster material is equal to or less than said first channel width.

45. The device of embodiment 44, wherein said bolster material has a width between a first lateral edge and a second lateral edge, and wherein said width of said bolster material is less than said first channel width.

46. The device of any one of embodiments 37 to 45, wherein said compressible layer comprises a multilayer construct, comprising one or more layers of a bolster support material carried by a core material.

47. The device of embodiment 46, wherein said core material has a maximum width greater than a maximum width for said bolster support material.

48. The device of any one of embodiments 37 to 47, wherein said bolster material comprises:
    a first sheet portion carried on a first side of said compressible layer;
    a second sheet portion carried by a second side of said compressible layer; and
    a bridge portion connecting said first sheet portion to said second sheet portion.

49. The device of any one of embodiments 37 to 48, wherein said bolster material comprises one or more attachment members configured to releasably secure said bolster material to said compressible layer.

50. The device of embodiment 49, wherein said compressed portion of said compressible layer comprises one or more notches configured to receive and secure said attachment members of said bolster material.

51. The device of any one of embodiments 49 or 50, wherein said attachment members of said bolster material are detachable from the bolster material.

52. The device of any one of embodiments 37 to 51, wherein a portion of said bolster material and said detachable portion of said compressible layer are detachable from the tray.

53. The device of any one of embodiments 37 to 52, wherein said bolster material comprises a collagenous material.

54. The device of any one of embodiments 37 to 52, wherein said bolster comprises a bioresorbable synthetic polymer.

55. The device of any one of the preceding embodiments, wherein said tray comprises a first tray component defining a first portion of said guide channel affixed to a second tray component defining a second portion of said guide channel.

56. The device of embodiment 55, wherein said first tray component and said second tray component are joined by one or more friction fittings.

57. The device of any one of embodiments 55 or 56, wherein said channel wall comprise a recessed portion, wherein said recessed portion is formed by corresponding grooves on the first and second tray components.

58. The device of any one of embodiments 55 to 57, wherein a portion of said compressible later and a portion of said bolster material are secured between said first tray component and said second tray component.

59. A method of loading a bolster material onto a surgical stapling device, the method comprising:
    providing a surgical stapling device having a receiving area for receipt of a bolster material, the receiving area including a first surface and a second surface;
    providing a loading device according to any one of claims 1 to 58;
    removing the peelable protective cover, while the compressible layer and the bolster material are received in the tray with the bolster material in the guide channel; and
    contacting the receiving area with the adhesive layer to adhere the bolster material to the surgical stapling device. All publications cited herein are hereby incorporated herein by reference in their entirety as if each had been individually incorporated by reference and fully set forth.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A device for loading a surgical bolster material onto a surgical stapling device, said device comprising:
    a tray defining a guide channel for receipt of a bolster material to be applied to the surgical stapling device;
    a compressible layer having a compressed portion compressed by said tray, and an elongate detachable portion extending into said guide channel, said detachable portion detachable from said compressed portion, said elongate detachable portion comprising a first lateral edge opposite a second lateral edge, and wherein said first lateral edge and said second lateral edge are uncompressed by said tray;
    a bolster material carried by said compressible layer, wherein said bolster material comprises a first lateral edge and a second lateral edge opposite said first lateral edge, and wherein said first lateral edge of said bolster material and said second lateral edge of said bolster material are uncompressed by said tray;
    an adhesive layer on said bolster material and configured to adhere said bolster material to the stapler; and
    a peelable protective cover over said adhesive layer, said peelable protective cover peelable from said adhesive layer while said compressible layer and said bolster material are received in said tray with said bolster material in said guide channel.

2. The device of claim 1, wherein said adhesive layer comprises a first lateral edge and a second lateral edge, and wherein said first lateral edge of said adhesive layer and said second lateral edge of said adhesive layer are uncompressed by said tray.

3. The device of claim 1, wherein said bolster material comprises:
    a first sheet portion carried on a first side of said compressible layer;
    a second sheet portion carried by a second side of said compressible layer; and a bridge portion connecting said first sheet portion to said second sheet portion.

4. The device of claim 1, wherein said compressible layer comprises a weakened region between said compressed portion and said detachable portion.

5. The device of claim 1, wherein said guide channel is defined by a channel wall, wherein said channel wall includes one or more recessed portions, said guide channel having a first channel width between opposing faces of said channel wall outside of said recessed portions, a second channel width between opposing portions of said channel wall within said recessed portions, and wherein said second channel width is greater than said first channel width.

6. The device of claim 5, wherein said detachable portion of said compressible layer has a width between a first elongate lateral edge and a second elongate lateral edge, and wherein said compressible layer width is less than said second channel width.

7. The device of claim 6, wherein said detachable portion width is greater than said first channel width, such that a portion of said compressible layer rests within said one or more recessed portions.

8. The device of claim 5, wherein said bolster material has a width between said first lateral edge and said second lateral edge, and wherein said width of said bolster material is equal to or less than said first channel width.

9. The device of claim 8, wherein said bolster material has a width between said first lateral edge and said second lateral edge, and wherein said width of said bolster material is less than said first channel width.

10. The device of claim 1, wherein said compressible layer comprises a multilayer construct, comprising one or more layers of a bolster support material carried by a core material.

11. The device of claim 10, wherein said core material has a maximum width greater than a maximum width for said bolster support material.

12. The device of claim 1, wherein said bolster material comprises one or more attachment members configured to releasably secure said bolster material to said compressible layer.

13. The device of claim 12, wherein said secured portion of said compressible layer comprises one or more notches configured to receive and secure said attachment members of said bolster material.

14. The device of claim 12, wherein said attachment members of said bolster material are detachable from a region of the bolster material positioned in said guide channel.

15. The device of claim 1, wherein a portion of said bolster material and said detachable portion of said compressible layer are detachable from the tray.

16. The device of claim 1, wherein said bolster material comprises a collagenous material.

17. The device of claim 1, wherein said bolster comprises a bioresorbable synthetic polymer.

18. The device of claim 1, wherein said tray comprises a first tray component defining a first portion of said guide channel affixed to a second tray component defining a second portion of said guide channel.

19. The device of claim 18, wherein said first tray component and said second tray component are joined by one or more friction fittings.

20. The device of claim 18, wherein said guide channel comprises a channel wall, wherein said channel wall comprise a recessed portion, wherein said recessed portion is formed by corresponding grooves on the first and second tray components.

21. The device of claim 18, wherein a portion of said compressible layer's and a portion of said bolster material are secured between said first tray component and said second tray component.

22. A method of loading a bolster material onto a surgical stapling device, the method comprising:
   providing a surgical stapling device having a receiving area for receipt of a bolster material, the receiving area including a first surface and a second surface;
   providing a device for loading a surgical bolster material onto a surgical stapling device according to claim 1;
   removing the peelable protective cover, while the compressible layer and the bolster material are received in the tray with the bolster material in the guide channel; and
   contacting the receiving area with the adhesive layer to adhere the bolster material to the surgical stapling device.

* * * * *